US008394360B2

(12) United States Patent
Kato et al.

(10) Patent No.: US 8,394,360 B2
(45) Date of Patent: Mar. 12, 2013

(54) ADDITIVE FOR HAIR COSMETIC PREPARATION, HAIR COSMETIC PREPARATION, AND METHOD FOR PRODUCING ADDITIVE FOR HAIR COSMETIC PREPARATION

(75) Inventors: Aiko Kato, Tokyo (JP); Hisao Takeda, Tokyo (JP)

(73) Assignee: Hymo Corporation, Tokyo (JP)

( * ) Notice: Subject to any disclaimer, the term of this patent is extended or adjusted under 35 U.S.C. 154(b) by 0 days.

(21) Appl. No.: 13/057,445

(22) PCT Filed: Aug. 6, 2009

(86) PCT No.: PCT/JP2009/063940
§ 371 (c)(1),
(2), (4) Date: Mar. 15, 2011

(87) PCT Pub. No.: WO2010/016543
PCT Pub. Date: Feb. 11, 2010

(65) Prior Publication Data

US 2011/0171154 A1 Jul. 14, 2011

(30) Foreign Application Priority Data

Aug. 8, 2008 (JP) ................................ 2008-204911

(51) Int. Cl.
*A61K 8/73* (2006.01)

(52) U.S. Cl. .............. 424/70.13; 424/70.11; 424/70.21; 424/70.22; 424/70.27; 424/70.31

(58) Field of Classification Search ....................... None
See application file for complete search history.

(56) References Cited

FOREIGN PATENT DOCUMENTS

| | | | |
|---|---|---|---|
| JP | 54-083987 | A | 7/1979 |
| JP | 2-180911 | A | 7/1990 |
| JP | 5-194673 | A | 8/1993 |
| JP | 2008-509250 | A | 3/2008 |
| JP | 2009-242371 | A | 10/2009 |

OTHER PUBLICATIONS

Lu et al "Study on the Synthesis and Application of Starch-graft-poly(AM-co-DADMAC) by using a complex Initiation System of CS-KPS"; Starch 56 (2004), p. 138-143.*
Meister et al "Synthesis and Properties of Several Cationic Graft Copolymers of Lignin" Marcomolecules, 1992, 25, p. 611-616.*
International Search Report mailed Nov. 17, 2009 for corresponding App No. PCT/JP2009/063940.
International Preliminary Report on Patentability mailed Mar. 17, 2011 for corresponding App No. PCT/JP2009/063940.

* cited by examiner

*Primary Examiner* — Bethany Barham
(74) *Attorney, Agent, or Firm* — Wolf, Greenfield & Sacks, P.C.

(57) ABSTRACT

The present invention provides an additive for a hair cosmetic preparation and a hair cosmetic preparation containing the additive that can give a supple feel to the finished hair. The additive for a hair cosmetic preparation contains a graft copolymer obtainable by graft-copolymerizing a cationic water-soluble monomer and a nonionic water-soluble monomer in an aqueous solution containing either one or both of a natural polymer and a natural polymer derivative that have an OH group.

20 Claims, No Drawings

ADDITIVE FOR HAIR COSMETIC PREPARATION, HAIR COSMETIC PREPARATION, AND METHOD FOR PRODUCING ADDITIVE FOR HAIR COSMETIC PREPARATION

RELATED APPLICATIONS

This application is a national stage filing under 35 U.S.C. §371 of International Application No. PCT/JP2009/063940, filed Aug. 6, 2009, which claims the benefit of Japanese Patent Application No. 2008-204911, filed Aug. 8, 2008. The contents of each of these applications are incorporated herein by reference in their entireties for all purposes.

TECHNICAL FIELD

The present invention relates to an additive for a hair cosmetic preparation, a hair cosmetic preparation, and a method for producing an additive for a hair cosmetic preparation.

BACKGROUND ART

Hair cosmetic preparations such as shampoos, rinses, and various hair styling agents are used to give the hair a desired texture and the like. As an ingredient of such a hair cosmetic preparation, a nonionic polymer, an anionic polymer, a cationic polymer, or the like is used.

Examples of the nonionic polymer include polyvinylpyrrolidone and poly(vinyl methyl ether).

Examples of the anionic polymer include a polymer of a vinylcarboxylic acid such as acrylic acid or methacrylic acid. Unlike a nonionic polymer, an anionic polymer is less likely to be affected by humidity.

As the cationic polymer, a polymer obtainable by reacting a cationizing agent such as glycidylpropyltrimethylammonium chloride with cellulose, guar gum, and the like (for example, polyquaternium-10) is widely used.

As other synthetic polymers, a diallyldimethylammonium chloride homopolymer (for example, polyquaternium-6), an acrylamide/diallyldimethylammonium chloride copolymer (for example, polyquaternium-7), and the like are used.

Also, with regard to a method for preparing a graft copolymer of a water-soluble monomer and polysaccharide, a method in which reactions are carried out in a solvent in which polysaccharide is not dissolved (refer to Patent Document 1), a method in which the above materials are polymerized by irradiation with electron beam in the state of near-solid phase (refer to Patent Document 2), and the like are disclosed.

Patent Document 1: Japanese Patent Laid-Open No. 54-83987

Patent Document 2: National Publication of International Patent Application No. 2008-509250

SUMMARY OF THE INVENTION

Problems to be Solved by the Invention

However, polyvinylpyrrolidone, which is used as a nonionic polymer, is susceptible to humidity conditions. Thus, while a film is hard and prone to cause a flaking phenomenon before absorbing moisture, it becomes extremely flexible and causes a blocking phenomenon in conditions of high temperature and humidity. As a result, there is a risk that the strands of hair stick together, making brushing difficult. Such an impact of humidity is much more noticeable on poly(vinyl methyl ether), which is used as a nonionic polymer.

When an anionic polymer is used as a hair cosmetic preparation, a film of anionic polymer is generally hard. Thus, while it has a high hair-styling effect, there is a problem of brittleness with the risk of causing a flaking phenomenon. Further, because it is anionic, addition of a cationic substance is limited, which raises a concern that a solidification phenomenon may be caused by a conditioning agent (cationic) and the like used during hair washing.

As to a cationic polymer, it has room for improvement considering that it makes the hair bristly and stiff when continuously used as an ingredient of a hair cosmetic preparation.

A synthetic polymer such as a diallyldimethylammonium chloride homopolymer (for example, polyquaternium-6) or an acrylamide/diallyldimethylammonium chloride copolymer (for example, polyquaternium-7) has room for improvement considering that, for example when polyquaternium-7 is added to a shampoo and the like, it gives a slimy feeling during shampooing.

Both of the preparation methods disclosed in Patent Documents 1 and 2 have the drawback that the reaction rate tends to be low. Also, when copolymerizing a plurality of monomers with different reactivity ratios, easily-polymerizable monomers are added continuously or sequentially to make the composition of the copolymer uniform; however, such a reaction is difficult to be carried out in a nonuniform system.

The present invention has been accomplished in view of the foregoing circumstance. A principal object of the present invention is to provide an additive for a hair cosmetic preparation and a hair cosmetic preparation containing the additive that give a supple feel to the finished hair.

Means for Solving the Problems

The present inventors conducted an intensive research to solve the aforementioned problems. As a result, they have found that an additive for a hair cosmetic preparation that is obtainable by dissolving a natural polymer having an OH group and/or a natural polymer derivative having an OH group in water and then graft-copolymerizing cationic and nonionic water-soluble monomers in the aqueous medium can give a supple feel to the finished hair, thereby completing the present invention.

That is, the present invention is as follows;

[1]

An additive for a hair cosmetic preparation comprising a graft copolymer obtainable by graft-copolymerizing a cationic water-soluble monomer and a nonionic water-soluble monomer in an aqueous solution comprising a natural polymer having an OH group and/or a natural polymer derivative having an OH group.

[2]

The additive for the hair cosmetic preparation according to the aforementioned [1], wherein a content of the cationic water-soluble monomer in the water-soluble monomers is from 5 to 90 mol %, and a content of the nonionic water-soluble monomer in the water-soluble monomers is from 10 to 95 mol %.

[3]

The additive for the hair cosmetic preparation according to the aforementioned [1] or [2], wherein the cationic water-soluble monomer is at least diallyldimethylammonium chloride, and the nonionic water-soluble monomer is at least acrylamide.

[4]

The additive for the hair cosmetic preparation according to any one of the aforementioned [1] to [3], wherein the natural polymer is one or more selected from the group consisting of guar gum, locust bean gum, and sericin.

[5]

The additive for the hair cosmetic preparation according to any one of the aforementioned [1] to [4], wherein the natural polymer derivative is one or more selected from the group consisting of hydroxyethyl cellulose, hydroxypropyl cellulose, hydroxypropyl methylcellulose, and hydroxypropyl guar gum.

[6]

The additive for the hair cosmetic preparation according to any one of the aforementioned [1] to [5], wherein a viscosity of a 2% aqueous solution of the natural polymer or the natural polymer derivative is 20,000 mPa·s or less at 25° C.

[7]

The additive for the hair cosmetic preparation according to any one of the aforementioned [1] to [6], wherein a mass ratio (A/B) of (A) a total amount of the natural polymer and/or the natural polymer derivative to (B) a total amount of the water-soluble monomer is from 5/95 to 80/20.

[8]

The additive for the hair cosmetic preparation according to any one of the aforementioned [1] to [7], wherein a total concentration of the natural polymer, the natural polymer derivative, and the water-soluble monomer in a reaction solution of the graft copolymer is from 10 to 50% by mass.

[9]

The additive for the hair cosmetic preparation according to any one of the aforementioned [1] to [8], wherein a weight-average molecular weight of the graft copolymer is from 10,000 to 3,000,000.

[10]

The additive for the hair cosmetic preparation according to any one of the aforementioned [1] to [9], wherein the graft copolymer is obtainable by performing a polymerization reaction at 50° C. or higher using a persulfate as an initiator.

[11]

The additive for the hair cosmetic preparation according to the aforementioned [3], wherein the graft copolymer is obtainable by performing graft copolymerization while adding at least a part of an amount of the acrylamide continuously or sequentially.

[12]

A hair cosmetic preparation comprising the additive for the hair cosmetic preparation according to any one of the aforementioned [1] to [11].

[13]

The hair cosmetic preparation according to the aforementioned [12], wherein the hair cosmetic preparation is a rinse, a conditioner, a treatment agent, a hair styling agent, a perm lotion, or a hair dye.

[14]

The hair cosmetic preparation according to the aforementioned [12], wherein the hair cosmetic preparation is a shampoo, and the content of the cationic water-soluble monomer in the water-soluble monomers is within a range of from 5 to 30 mol %.

[15]

A method for producing an additive for a hair cosmetic preparation comprising the steps of:

dissolving a natural polymer having an OH group and/or a natural polymer derivative having an OH group in water to prepare an aqueous solution; and graft-copolymerizing a cationic water-soluble monomer and a nonionic water-soluble monomer in the aqueous solution.

[16]

The method for producing the additive for the hair cosmetic preparation according to the aforementioned [15], wherein a chain transfer agent is added to the aqueous solution in the step of graft copolymerization.

[17]

The method for producing the additive for the hair cosmetic preparation according to the aforementioned [15] or [16], wherein a persulfate is added to the aqueous solution as an initiator in the step of graft copolymerization.

[18]

The method for producing the additive for the hair cosmetic preparation according to any one of the aforementioned [15] to [17], wherein the cationic water-soluble monomer is at least diallyldimethylammonium chloride, the nonionic water-soluble monomer is at least acrylamide, and at least a part of an amount of the acrylamide is continuously or sequentially added to the aqueous solution in the step of graft copolymerization.

DESCRIPTION OF THE PREFERRED EMBODIMENT

Hereinbelow, embodiments for carrying out the present invention (hereinbelow, simply referred to as "the present embodiment") will be described. It is to be noted that the present embodiment given below is an example of the present invention, and the present invention is not intended to be restricted to the content described below. The present invention can be appropriately modified and practiced within the scope of the gist of the invention.

The additive for a hair cosmetic preparation according to the present embodiment contains a graft copolymer obtainable by graft-copolymerizing a cationic water-soluble monomer and a nonionic water-soluble monomer in an aqueous solution containing a natural polymer having an OH group and/or a natural polymer derivative having an OH group. The graft copolymer is obtainable by dissolving either one or both of a natural polymer and a natural polymer derivative that have an OH group in water to prepare an aqueous solution, and then graft-copolymerizing a cationic water-soluble monomer and a nonionic water-soluble monomer in the aqueous solution in a substantially uniform state. In the graft copolymerization reaction, a small amount of a water-soluble organic solvent such as an alcohol can be mixed into the aqueous solution as needed.

Although the content of the cationic water-soluble monomer in the water-soluble monomers is not particularly limited, it is preferably within the range of from 5 to 90 mol %. Although the content of the nonionic water-soluble monomer in the water-soluble monomers is not particularly limited, it is preferably within the range of from 10 to 95 mol %. As the nonionic water-soluble monomer is contained in an amount of from 10 mol % or more, smoothness can be added to the hair treated with a hair cosmetic preparation containing the additive for the hair cosmetic preparation according to the present embodiment, giving better texture to the finished hair. By setting the content of the nonionic water-soluble monomer as above, no stickiness is observed in the treated hair, and hair tangling can be prevented even in high humidity conditions.

The natural polymer and the natural polymer derivative are preferably highly soluble in water since reactions are carried out in a substantially uniform state in aqueous solution. Examples of the natural polymer may include starches, guar gum, locust bean gum, xanthan gum, chitosan, carrageenan, gellan gum, pullulan, mannan, fenugreek, sericin and the like. Among them, guar gum, locust bean gum, and sericin are preferable from the viewpoint of solubility.

Examples of the natural polymer derivative may include methylcellulose, hydroxyethyl cellulose, hydroxypropyl cellulose, hydroxypropyl methylcellulose, hydroxyethyl guar gum, hydroxypropyl guar gum and the like. Among them, hydroxyethyl cellulose, hydroxypropyl cellulose, hydroxypropyl methylcellulose, and hydroxypropyl guar gum are preferable from the viewpoint of solubility, and among them, hydroxyethyl cellulose is more preferable. A plurality of these natural polymers and natural polymer derivatives can also be used in combination.

Although the molecular weight of the natural polymer or the natural polymer derivative is not particularly limited, the viscosity of a 2% aqueous solution is preferably 20,000 mPa·s or less at 25° C. since graft copolymerization is performed in the state of substantially uniform aqueous solution. By setting the viscosity of a 2% aqueous solution at 20,000 mPa·s or less at 25° C., marked elevation in the viscosity of the solution having the natural polymer and/or the natural polymer dissolved therein can be prevented, enabling uniform graft copolymerization. For example, in the case of hydroxyethyl cellulose, which is a preferable natural polymer derivative, the viscosity of a 2% aqueous solution is more preferably within the range of from 100 to 10,000 mPa·s in consideration of the viscosity of a reaction liquid. The viscosity of a 2% aqueous solution refers to a viscosity of deionized water containing a water-soluble polymer dissolved at a concentration of 2% by mass, which can be measured by a B type viscometer.

The mass ratio (A/B) of (A) the total amount of the natural polymer and/or the natural polymer derivative to (B) the total amount of the water-soluble monomer is preferably from 5/95 to 80/20, more preferably from 5/95 to 50/50. By setting the mass ratio (A/B) within the above-described range, the natural polymer and the synthetic polymer can exert synergistic effects when prepared as an additive for the hair cosmetic preparation. Herein, (A) the total amount of the natural polymer and/or the natural polymer derivative refers to the total amount of the natural polymer and the natural polymer derivative when both are used in combination, the total amount of the natural polymer when it is used alone, or the total amount of the natural polymer derivative when it is used alone.

Graft copolymerization is normally performed while stirring to carry out a uniform reaction. Thus, an excessively high reaction concentration makes stirring difficult, while an excessively low reaction concentration produces a final product with a low concentration, which will result in increased transportation costs. From the above perspective, the reaction concentration is preferably from 10 to 50% by mass, more preferably from 10 to 30% by mass, as the total concentration of the natural polymer and/or the natural polymer derivative and the water-soluble monomer.

Among the cationic water-soluble monomers, examples of a cationic monomer containing a tertiary amino group may include dimethylaminoethyl(meth)acrylate, diethylaminoethyl(meth)acrylate, dimethylaminopropyl(meth)acrylamide, diethylaminopropyl(meth)acrylamide, and a salt of these monomers. Examples of a cationic monomer containing a quaternary ammonium base may include (meth)acryloyloxyethyltrimethylammonium chloride, (meth)acryloyloxyethyldimethylbenzylammonium chloride, (meth)acryloylaminopropyltrimethylammonium chloride, (meth)acryloylaminopropyldimethylbenzylammonium chloride, and (meth)acryloyloxy-2-hydroxypropyltrimethylammonium chloride. Further, examples thereof may include allylamine, diallylmethylamine, and a salt of these amines, and diallyldimethylammonium chloride. Among them, diallyldimethylammonium chloride is more preferable from the viewpoint of stability and safety of a polymer. A plurality of these cationic water-soluble monomers can also be used in combination.

Examples of the nonionic water-soluble monomer to be copolymerized with the cationic water-soluble monomer may include (meth)acrylamide, dimethylacrylamide, diethylacrylamide, isopropylacrylamide, hydroxyethylacrylamide, vinylpyrrolidone, vinylformamide, and vinylacetamide. Acrylamide is more preferable from the viewpoint of easiness of the polymerization reaction. A plurality of these nonionic water-soluble monomers can also be used in combination. Further, as long as a graft polymer is water-soluble, a hydrophobic monomer such as styrene and (meth)acrylic acid alkyl ester can be copolymerized.

The temperature at which graft copolymerization is performed needs to be a temperature at which the natural polymer and/or the natural polymer derivative can be dissolved in water. Although the temperature varies depending on the natural polymer and/or the natural polymer derivative used, graft copolymerization is normally performed at a temperature within the range of from 30 to 95° C.

To initiate polymerization, a radical polymerization initiator is used. The initiator is preferably water-soluble, and any of an azo-based initiator, a redox-based initiator, a persulfate-based initiator, and a peroxide-based initiator can be used.

Examples of the water-soluble azo-based initiator may include 2,2'-azobis(2-methylpropionamidine)dihydrochloride, 2,2'-azobis[2-(2-imidazoline-2-yl)propane]dihydrochloride, and 4,4'-azobis(4-cyanovaleric acid).

Examples of the redox-based initiator may include a combination of a polymerization initiator such as a persulfate including ammonium peroxodisulfate and a reducing agent. Examples of the reducing agent may include sulfite such as sodium sulfite and sodium bisulfite, trimethylamine, and tetramethylethylenediamine.

Examples of the persulfate-based initiator may include a persulfate such as ammonium peroxodisulfate or potassium persulfate. Examples of the peroxide-based initiator may include peroxide such as hydrogen peroxide.

Among them, a persulfate initiator is preferable considering that it allows efficient graft copolymerization. When using a persulfate, polymerization reaction is preferably performed at 50° C. or higher. When guar gum, hydroxypropyl guar gum, or the like whose aqueous solution is considered to have a relatively high viscosity is used, it is sometimes difficult to carry out graft copolymerization efficiently. However, according to the present embodiment, use of a persulfate as an initiator enables efficient graft copolymerization even when a substance whose aqueous solution has a relatively high viscosity such as ones described as above is employed.

According to the present embodiment, cationic and nonionic water-soluble monomers are graft copolymerized in the presence of a natural polymer having an OH group and/or a natural polymer derivative dissolved in water. When carrying out this graft copolymerization, a plurality of water-soluble monomers may be prepared in advance all at once and subjected to nitrogen substitution, after which a polymerization initiator may be added to initiate polymerization. Alternatively, after addition of the polymerization initiator, a part or entire amount of the water-soluble monomer may be added little by little continuously or sequentially while stirring.

Particularly when a plurality of monomers to be copolymerized have different ratios of copolymerizability, it is preferable to add a part of the amount of easily-polymerizable monomers continuously or sequentially to make the composition of the copolymer uniform.

Particularly when copolymerizing diallyldimethylammonium chloride and acrylamide, it is preferable to add at least a part of the amount of acrylamide continuously or sequentially to an aqueous solution. Due to a large difference between the polymerization rate of diallyldimethylammonium and that of acrylamide, there is a tendency that, when the monomer is prepared in advance all at once, only the polymerization of acrylamide proceeds and diallyldimethylammonium remains as a monomer. Consequently, there is a tendency that remaining diallyldimethylammonium undergoes homopolymerization, and as a result graft chains of acrylamide and graft chains of diallyldimethylammonium chloride are separately produced. In view of the above, the aforementioned phenomenon can be effectively prevented by adding acrylamide continuously or sequentially.

The weight-average molecular weight of the graft polymer as measured by gel permeation chromatography with multi-angle light scattering (GPC-MALS) is preferably from 10,000 to 3,000,000, more preferably from 20,000 to 2,000,000. The compatibility of the graft polymer with various ingredients used in a hair cosmetic preparation can be improved when the weight-average molecular weight is 3,000,000 or less. A sufficient effect of addition of the graft polymer can be obtainable when the weight-average molecular weight is 10,000 or more. In order to adjust the molecular weight, a necessary amount of a chain transfer agent can be added during polymerization. As a chain transfer agent, any can be selected from compounds having chain transferability that are generally used such as isopropyl alcohol, mercaptoethanol, sodium gluconate, sodium formate, and sodium hypophosphite.

The additive for the hair cosmetic preparation according to the present embodiment can be incorporated in various hair cosmetic preparations. The hair cosmetic preparation containing the additive for the hair cosmetic preparation according to the present embodiment can be favorably used as, for example, a rinse, a conditioner, a treatment agent, a hair styling agent, a perm lotion, or a hair dye. Further, by appropriately adjusting the content of the additive for the hair cosmetic preparation, the hair cosmetic preparation can also be favorably used as a shampoo.

When the additive is incorporated in a shampoo, there are cases in which, when a cation-equivalent value is too high, the cation forms a complex with an anionic surfactant, which is the main ingredient of the composition of a shampoo, whereby the additive becomes insoluble and generation of white turbidity is prevented. From this perspective, when the additive for the hair cosmetic preparation according to the present embodiment is mixed in a shampoo, the content of a cationic water-soluble monomer in the water-soluble monomers is preferably within the range of from 5 to 30 mol %.

When the additive for the hair cosmetic preparation according to the present embodiment is used in a rinse, a conditioner, or a treatment agent, considering that the main ingredient of these agents is a cationic surfactant, the content of a cationic water-soluble monomer in the water-soluble monomers is selected within the range of from 5 to 90 mol % according to the effect expected in a hair cosmetic preparation; however, the content is more preferably within the range of from 5 to 60 mol %.

When the additive for the hair cosmetic preparation according to the present embodiment is used in a hair styling agent, a perm lotion, or a hair dye, considering that these agents often do not contain an ionic surfactant, the ratio of a cationic water-soluble monomer in the water-soluble monomers is similarly selected within the range of from 5 to 90 mol % according to the desired effect. While the hair styling agent includes formulations such as a liquid, a cream, an emulsion, a spray, a foam, and a gel, the additive for the hair cosmetic preparation according to the present embodiment can be used in any formulation.

The additive for the hair cosmetic preparation according to the present embodiment is normally added to a hair cosmetic preparation in an amount of from 0.05 to 5% by mass. However, the amount to be added is not particularly limited as long as it is within such a range that the effect expected in each hair cosmetic preparation can be exerted.

According to use of a hair cosmetic preparation, known additives such as an anionic surfactant, a cationic surfactant, a betaine surfactant, and a nonionic surfactant can be added to the hair cosmetic preparation as other ingredients.

Examples of the anionic surfactant may include N-fatty acid acyl-L-glutamate such as sodium lauroyl methylalanine, triethanolamine cocoyl glutamate, sodium N-lauryl-L-glutamate, triethanolamine N-coconut oil fatty acid-L-glutamate, sodium N-myristic acid acyl-L-glutamate, and sodium N-mixed fatty acid acyl-L-glutamate; N-fatty acid-N-methyltaurate such as sodium methyltaurate laurate, sodium coconut oil fatty acid methyltaurate; a salt of N-fatty acid sarcosine condensation product such as sodium lauroylsarcosine, and sodium cocoylsarcosine; and a N-acyl fatty acid-N-methyl-β-alanine salt such as sodium acylsarcosine, acyl glutamate, sodium acyl-β-alanine, acyl taurate, lauryl sulfate, polyoxyethylene lauryl ether sulfate, sodium N-coconoyl-N-methyl-β-alanine and sodium N-myristoyl-N-methyl-β-alanine.

Examples of the cationic surfactant may include lauryltrimethylammonium chloride, stearyltrimethylammonium chloride, distearyldimethylammonium chloride, and stearyldimethylbenzylammonium chloride.

Examples of the betaine surfactant may include betaine lauryldimethylaminoacetate, cocoacidopropyl betaine, dimethyllauryl betaine, bis(2-hydroxyethyl)lauryl betaine, coconut oil fatty acid amidopropyl betaine, sodium cocoamphoacetate, cyclohexyl lauryl amine oxide, dimethyl lauryl amine oxide, bis(2-hydroxyethyl)lauryl amine oxide, oleyl betaine, stearyl betaine, myristyl betaine, and stearyl dihydroxyethyl betaine.

Examples of the nonionic surfactant may include glyceryl monostearate, sorbitan monopalmitate, polyoxyethylene cetyl ether, polyoxyethylene sorbitan monolaurate, sorbitan fatty acid ester, glycerol fatty acid ester, polyoxyethylene sorbitan fatty acid ester, polyethylene glycol fatty acid ester, polyoxyethylene alkyl ether, polyoxyethylene alkylphenyl ether, polyoxyethylene castor oil, polyoxyethylene hydrogenated castor oil, fatty acid alkanolamide, stearic acid diethanolamide, coconut oil fatty acid diethanolamide, sorbitan sesquioleate, and polyoxyethylene stearyl ether.

Further, other arbitrary ingredients can be incorporated as needed as long as they do not affect the effect of the preset embodiment. Examples of such an arbitrary ingredient may include higher fatty acids and derivatives thereof, water-soluble polymers, and various ultraviolet absorbers.

Examples of the higher fatty acids and derivatives thereof may include hydrocarbons such as liquid paraffin, petrolatum, solid paraffin, squalane, and olefin oligomer; alcohols such as ethanol, lauryl alcohol, cetyl alcohol, stearyl alcohol, behenyl alcohol, myristyl alcohol, oleyl alcohol, cetostearyl alcohol, monostearyl glycerol ether, 2-decyltetradecynol, lanolin alcohol, cholesterol, phytosterol, hexyldodecanol, isostearyl alcohol, and octyl dodecanol; ester oils such as isopropyl myristate, octyldodecyl myristate, ethyldodecyl palmitate, stearyl stearate, glycol distearate, polyethylene glycol sorbitol tetraoleate, glyceryl monostearate, diethylpentanediol dineopentanoate, and hydrogenated castor oil polyethylene glycol; higher fatty acids such as lauric acid, myristic acid, palmitic acid, stearic acid, behenic (behenyl) acid, oleic acid, 1,2-hydroxystearic acid, undecylenic acid, tallic acid, lanolin fatty acid, isostearyl acid, linoleic acid, linolenic acid, γ-linolenic acid, and eicosapentaenoic acid; and derivatives thereof.

Examples of the water-soluble polymer may include natural water-soluble polymers including plant-derived polymers such as carrageenan, pectin, agar, quince seeds (Cydonia oblonga), algae colloid (brown algae extract), starch (rice, corn, potato, and wheat), and glycyrrhetinic acid, microorganism-derived polymers such as xanthan gum, dextran, and pullulan, and an animal-derived polymer such as collagen and gelatin; semi-synthetic water-soluble polymers including cellulose-based polymers such as methyl cellulose, ethyl cellulose, methyl hydroxypropyl cellulose, hydroxyethyl cellulose, cellulose sodium sulfate, hydroxypropyl cellulose, carboxymethylcellulose sodium, cationic cellulose, crystalline cellulose, and cellulose powder, and alginic acid polymers such as cationic guar gum, sodium alginate, and alginic acid propylene glycol ester; vinyl-based polymers such as polyvinyl alcohol, polyvinyl methyl ether, polyvinylpyrrolidone, and carboxyvinyl polymers (trade name "Carbopol"), polyoxyethylene-based polymers such as polyethylene glycols 20,000, 600,000, and 4,000,000; and polyethyleneimine.

Examples of various ultraviolet absorbers may include inorganic substances such as bentonite, magnesium aluminum silicate (veegum), laponite, hectorite, and silicic anhydride, silicones such as volatile silicone oil, silicone resin, silicone gum, alkyl modified silicone, polyethylene glycol addition silicone, and amino modified silicone, sequestering agents such as 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, and gluconic acid, 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazol, 2-(2'-hydroxy-5'-t-octylphenyl)benzotriazol, 2-(2'-hydroxy-5'-methylphenyl)benzotriazol, dibenzalazine, dianisoyl methane, 4-methoxy-4'-t-butyldibenzoylmethane, and 5-(3,3-dimethyl-2-norbornylidene)-3-pentane-2-one, a benzoic acid-based ultraviolet absorber, an anthranilic acid-based ultraviolet absorber, a salicylic acid-based ultraviolet absorber, a cinnamic acid-based ultraviolet absorber, and a benzophenone-based ultraviolet absorber.

Examples of other arbitrary ingredients may include humectants such as (poly)ethylene glycol, (poly)propylene glycol, glycerin, 1,3-butylene glycol, maltitol, sorbitol, chondroitin sulfate, hyaluronic acid, atelocollagen, cholesteryl-1, 2-hydroxystearate, sodium lactate, bile salt, dl-pyrrolidone carboxylate, short-chain soluble collagen, and sodium aspartate, antiseptics such as hinokitiol, hexachlorophene, benzalkonium chloride, trichlorocarbanilide, and pitionol, vasodilators such as carpronium chloride, refreshings agent such as menthols, stimulators such as benzyl nicotinate, vitamins such as vitamin A, B, C, D and E, disinfecting antiseptic agents such as chlorhexidine gluconate, isopropyl methyl phenol, and p-oxybenzoate ester, protein hydrolysate, amino acids, a plant extract, chelating agents such as EDTA-Na, pH adjusters such as succinic acid, sodium succinate, and triethanolamine, a foam enhancer, a foaming agent, a foam stabilizer, a propellant such as liquefied petroleum gas and dimethyl ether in the case of an aerosol product, a sequestering agent, an antifungal agent, a disinfectant, an emulsifier, a conditioning agent, a viscosity enhancer, an antioxidant, a solubilizing agent, a rosin, a hydrotrope, a hair growth agent, a crude drug, a coloring agent, and a fragrance.

Further, a known cationic, anionic, amphoteric, or nonionic synthetic, semi-synthetic, or natural polymer different from the embodiment of the present invention can also be used in combination.

Examples of the cationic polymer may include, for example, vinyl imidazolium chloride/vinylpyrrolidone copolymers such as trade names "Luviquat FC 370", "Luviquat FC 550", "Luviquat FC 905", "Luviquat HM 552", and "Luviquat Mono CP" (all are manufactured by BASF), hydroxyethyl cellulose/dimethyldiallylammonium chloride such as trade name "Celquat H-100 (a viscosity of 1,000 mPa·s)" and trade name "Celquat L-200 (a viscosity of 100 mPa·s)" (both are manufactured by National Starch), diallyldimethylammonium chloride homopolymers such as trade names "Merquat 100" and "Merquat 550", diallyldimethylammonium chloride/acrylamide copolymers and terpolymers containing these homopolymers and copolymers (for example, trade name "Merquat 3331"), copolymers or terpolymers containing methacrylamidopropyl trimethylammonium chloride (for example, trade name "Merquat 2001") (all are manufactured by Nalco Company), vinylpyrrolidone/tertiary dimethylaminoethyl methacrylate copolymers such as trade names "Gafquat 734", "Gafquat 755N", and "Gafquat 755" (all are manufactured by International Specialty Products, Inc. (ISP)), polyvinylpyrrolidone/alkylaminoacrylate copolymers such as trade name "Luviflex" (manufactured by BASF) and trade names "Copolymer 845", "Copolymer 937", and "Copolymer 958" (all are manufactured by ISP), polyvinylpyrrolidone/alkylaminoacrylate/vinyl caprolactam copolymers such as trade name "Copolymer VC-713" (manufactured by ISP), vinylpyrrolidone/methacrylamidopropyl trimethylammonium chloride copolymers such as trade name "Gafquat HS-100" (manufactured by ISP), N,N-dimethylaminoethyl methacrylic acid diethyl sulfate, which is listed under the name of "polyquaternium-52" in an ingredient label, a N,N-dimethylacrylamide/polyethylene glycol dimethacrylate copolymer, an alkylacrylamide/acrylate/alkylaminoalkylacrylamide/polyet hylene glycol methacrylate copolymer such as the water-soluble polymer as described in Japanese Patent Laid-Open No. 2-180911, a N-propionylpolyethyleneimine/methylpolysiloxane copolymer, an acrylamide/acrylate/methacrylic acid alkyl ester/methoxypolyethylene glycol copolymer, and an acrylamide/acrylic acid alkyl ester copolymer.

Examples of the anionic polymer may include methyl vinyl ether/maleic anhydride alkyl half ester copolymers such as trade name "Gantrez ES-225", trade name "Gantrez ES-425", and trade name "Gantrez SP-215" (all are manufactured by ISP), vinyl acetate/crotonic acid copolymers such as trade name "Resyn 28-1310" (manufactured by National Starch) and trade name "Luviset CA" (manufactured by BASF), a vinyl acetate/crotonic acid/vinyl neodecanoate copolymer such as trade name "Resyn 28-2930" (manufactured by National Starch), vinyl acetate/crotonic acid/vinyl propionate copolymers such as trade name "Luviset CAP" (manufactured by BASF), vinyl acetate/monobutyl maleate/isobornyl acrylate copolymers such as trade name "Advantage CP" (manufactured by ISP), (meth)acrylic acid/(meth)acrylic acid alkyl ester copolymers such as trade name "Plas cize L53P", trade name "Plas cize L-75CB", trade name "Plas cize L-9540B" (all are manufactured by Goo Chemical Co., Ltd.), and trade name "Diahold" (manufactured by Mitsubishi Chemical Corporation), acrylic acid/acrylic acid alkyl ester/alkylacrylamide copolymers such as trade names "Ultrahold 8" and "Ultraholdstrong" (both are manufactured by BASF), and trade name "Amphomer V-42" (manufactured by National Starch), polyvinylpyrrolidone/acrylate/(meth) acrylic acid copolymers such as trade name "Luviflex VBM35" (manufactured by BASF), and an urethane polymer, which is listed under the name of "polyurethane-1" in an ingredient label, such as a isophthalic acid/adipic acid/hexylene glycol/neopentyl glycol/dimethylol propionic acid/isophorone diisocyanate copolymer.

Examples of the amphoteric polymer may include N-methacryloyloxyethyl-N,N-dimethylammonium-α-N-methylcarboxybetaine/methacrylic acid alkyl ester copolymers such as trade names "Yukaformer SM", "Yukaformer 301", "Yukaformer 205S", "Yukaformer 201", and "Yukaformer W" (all are manufactured by Mitsubishi Chemical Corporation), and hydroxypropyl acrylate/butylaminoethyl methacrylate/acrylic acid octylamide copolymers such as trade names "Amphomer 28-4910" and "Amphomer LV-71" (both are manufactured by National Starch).

Examples of the nonionic polymer may include polyvinylpyrrolidone such as trade names "Luviskol K-12", "Luviskol K-17", "Luviskol K-30", "Luviskol K-60", "Luviskol K-80", and "Luviskol K-90" (all are manufactured by BASF), trade names "PVP K15", "PVP K30", "PVP K60", and "PVP K90" (all are manufactured by ISP), polyvinylpyrrolidone/vinyl acetate copolymers such as trade names "Luviskol VA28", "Luviskol VA37", "Luviskol VA55", "Luviskol VA64", "Luviskol VA73", and "Luviskol VA37E" (all are manufactured by BASF), trade names "PVP/VA E-735", "PVP/VA E-635", "PVP/VA E-535", "PVP/VA E-335", "PVP/VA S-630", and "PVP/VA W-735" (all are manufactured by ISP), and polyvinylpyrrolidone/vinyl acetate/vinyl propionate copolymers such as trade name "Luviskol VAP343" (manufactured by BASF), and vinyl acetate/N-vinyl-5-methyl-2-oxazoline copolymers such as trade name "Dowtex" (manufactured by The Dow Chemical Company).

The method for producing the additive for the hair cosmetic preparation according to the present embodiment includes the steps of dissolving a natural polymer having an OH group and/or a natural polymer derivative having an OH group in water to prepare an aqueous solution and graft-copolymerizing a cationic water-soluble monomer and a nonionic water-soluble monomer in the aforementioned aqueous solution.

It is preferable to add the aforementioned chain transfer agent to the aqueous solution in the step of graft copolymerization. The molecular weight of the resulting graft copolymer can be adjusted by adding a necessary amount of the chain transfer agent during graft polymerization.

It is preferable to add the aforementioned persulfate to the aqueous solution as an initiator in the step of graft copolymerization. Graft copolymerization can be efficiently carried out by using a persulfate as an initiator. Specifically, it is more preferable to perform graft copolymerization at 50° C. or higher.

Particularly when the cationic water-soluble monomer is at least diallyldimethylammonium chloride and the nonionic water-soluble monomer is at least acrylamide, it is preferable to add at least a part of the amount of the acrylamide continuously or sequentially to the aqueous solution in the step of graft copolymerization. The composition of diallyldimethylammonium chloride and acrylamide in a graft copolymer can be made uniform by adding acrylamide, which has a faster polymerization rate, continuously or sequentially.

The hair cosmetic preparation containing the additive for the hair cosmetic preparation obtainable by graft-copolymerizing cationic and nonionic water-soluble monomers with a natural polymer having an OH group and/or a natural polymer derivative having an OH group in an aqueous medium according to the present embodiment provides excellent finish. Moreover, a smaller amount of the above hair cosmetic preparation needs to be added compared with a widely-used polymer obtainable by reacting glycidylpropyltrimethylammonium chloride with hydroxyethyl cellulose (polyquaternium-10).

Also, in the case of an acrylamide/diallyldimethylammonium chloride copolymer (polyquaternium-7), it creates a slimy feeling upon use when the addition amount is increased. In contrast, the additive for the hair cosmetic preparation according to the present embodiment does not produce an unpleasant feeling such as a slimy feeling even when the addition amount is increased. Therefore, no limitation is imposed on the addition amount of the additive for the hair cosmetic preparation in the formulation of a hair cosmetic preparation.

According to the present embodiment, cationic and nonionic water-soluble monomers are graft copolymerized with a natural polymer having an OH group and/or a natural polymer derivative having an OH group. The hair treated with a hair cosmetic preparation containing an additive for the hair cosmetic preparation obtainable by graft polymerizing only a cationic water-soluble monomer has a sticky feeling; however, the hair treated with the hair cosmetic preparation according to the present embodiment, which contains a water-soluble monomer to be subjected to graft copolymerization that include a nonionic monomer, is provided with a smooth feeling, and the finished hair has excellent texture.

EXAMPLES

Hereinbelow, the present invention will be described further in detail with Examples; however, the present invention is not limited to the following Examples.

Example 1

Into a 500 mL four-neck separable flask equipped with a stirrer, a reflux cooling pipe, a monomer drip outlet, and a nitrogen introduction pipe, 126.99 g of deionized water, 10.06 g of a 50% by mass aqueous solution of acrylamide, 9.30 g of a 65% by mass aqueous solution of diallyldimethylammonium chloride, and 0.40 g of sodium gluconate were added, and a uniform mixture was prepared. Into the mixture thus obtained, 10.00 g of hydroxypropyl cellulose (manufactured by Wako Pure Chemical Industries, Ltd., the viscosity of a 2% aqueous solution at 25° C. as measured by a E type viscometer: 5.2 mPa·s) was added while stirring, and nitrogen was introduced through the nitrogen introduction pipe, and the internal temperature was adjusted at 45° C. using a constant temperature bath. Nitrogen was introduced for 30 minutes to this mixture, after which 1.50 g of a 10% by mass aqueous solution of 2,2'-azobis[2-(2-imidazoline-2-yl)propane]dihydrochloride was added to initiate polymerization.

Meanwhile, 37.85 g of a 50% by mass aqueous solution of acrylamide was added to 2.00 g of a 20% by mass aqueous solution of sodium gluconate to prepare a mixture. Polymerization was performed while adding the mixture thus obtained dropwise to the system prepared as above over five hours from immediately after initiation of the reaction. After five hours, 1.50 g of a 10% by mass aqueous solution of 2,2'-azobis[2-(2-imidazoline-2-yl)propane]dihydrochloride was further added and polymerization was carried out for further 17 hours, and then the reaction was terminated. The weight-average molecular weight was measured to be 190,000 by GPC-MALS under the following conditions: GPC-MALS measurement device; "DAWN HELEOS" manufactured by Wyatt Technology Corporation, separation column; "TSKgel G6000 PWXL-CP" manufactured by Tosoh Corporation, eluting solution; 0.5 M acetic acid+0.5 M sodium acetate buffer, flow rate; 0.5 mL/min, temperature; 25° C., sample concentration; 0.1% by mass, and injection volume; 100 μL. The product thus obtained was provided as "graft copolymer 1."

Example 2

Hydroxypropyl guar gum (manufactured by Sansho Co., Ltd., trade name "Jaguar HP-08", the viscosity of a 2% aqueous solution at 25° C. as measured by a B type viscometer: 35,000 mPa·s) was swollen and dissolved in deionized water so as to give a 10% by mass solution of hydroxypropyl guar gum. To the hydroxypropyl guar gum thus obtained, 1.0% by mass ammonium peroxodisulfate was added and the resulting mixture was heated to 65° C. to adjust the viscosity of a 2% aqueous solution to 12500 mPa·s. Into a reaction container similar to the one used in Example 1, 100 g of a 10% by mass hydroxypropyl guar gum solution with an adjusted molecular weight was put, and 39.42 g of deionized water, 8.04 g of a 50% by mass aqueous solution of acrylamide, 16.72 g of a 65% by mass aqueous solution of diallyldimethylammonium chloride, and 0.30 g of sodium formate were added, and a uniform mixture was prepared. Nitrogen was introduced through the nitrogen introduction pipe, and the internal temperature was adjusted at 65° C. using a constant temperature bath. Nitrogen was introduced for 30 minutes, after which 1.50 g of a 10% by mass aqueous solution of ammonium peroxodisulfate was added to initiate polymerization.

Meanwhile, 30.23 g of a 50% by mass aqueous solution of acrylamide was added to 2.00 g of a 15% by mass aqueous solution of sodium formate to prepare a mixture. Polymerization was performed while adding the mixture thus obtained dropwise to the system prepared as above over five hours from immediately after initiation of the reaction. After five hours, 1.50 g of a 10% by mass aqueous solution of ammonium peroxodisulfate was added and polymerization was continued for further 17 hours, and then the reaction was terminated. The weight-average molecular weight was measured to be 130,000 by GPC-MALS. The product thus obtained was provided as "graft polymer 2."

Example 3

Into a reaction container similar to the one used in Example 1, 126.99 g of deionized water, 10.06 g of a 50% by mass aqueous solution of acrylamide, 9.30 g of a 65% by mass aqueous solution of diallyldimethylammonium chloride, and 0.40 g of sodium gluconate were added, and a uniform mixture was prepared. While stirring, 10.00 g of hydroxyethyl cellulose (manufactured by Sumitomo Seika Chemicals Co., Ltd., the viscosity of a 2% aqueous solution at 25° C. as measured by a B type viscometer: 5340 mPa·s) were added, and then nitrogen was introduced through the nitrogen introduction pipe, and the internal temperature was adjusted at 65° C. using a constant temperature bath. Nitrogen was introduced for 30 minutes, after which 1.50 g of a 10% by mass aqueous solution of ammonium peroxodisulfate was added to initiate polymerization.

Meanwhile, 37.85 g of a 50% by mass aqueous solution of acrylamide was added to 2.00 g of a 20% by mass aqueous solution of sodium gluconate to prepare a mixture. Polymerization was performed while adding the mixture thus obtained dropwise to the system prepared as above over five hours from immediately after initiation of the reaction. After five hours, 1.50 g of a 10% by mass aqueous solution of ammonium peroxodisulfate was further added and polymerization was continued for further 17 hours, and then the reaction was terminated. The weight-average molecular weight was measured to be 850,000 by GPC-MALS. The product thus obtained was provided as "graft polymer 3."

Example 4

Into a reaction container similar to the one used in Example 1, 164.37 g of deionized water, 10.05 g of a 50% by mass aqueous solution of acrylamide, 20.90 g of a 65% by mass aqueous solution of diallyldimethylammonium chloride, and 0.075 g of sodium formate were added, and a uniform mixture was prepared. While stirring, 12.50 g of hydroxyethyl cellulose (manufactured by Wako Pure Chemical Industries, Ltd., the viscosity of a 2% aqueous solution at 25° C. as measured by a B type viscometer: 152 mPa·s) were added, and then nitrogen was introduced through the nitrogen introduction pipe, and the internal temperature was adjusted at 65° C. using a constant temperature bath. Nitrogen was introduced for one hour, after which 1.88 g of a 10% by mass aqueous solution of ammonium peroxodisulfate was added to initiate polymerization.

Meanwhile, 37.79 g of a 50% by mass aqueous solution of acrylamide was added to 0.50 g of a 15% by mass aqueous solution of sodium formate to prepare a mixture. Polymerization was performed while adding the mixture thus obtained dropwise to the system prepared as above over five hours from immediately after initiation of the reaction. After five hours, 1.88 g of a 10% by mass aqueous solution of ammonium peroxodisulfate was further added and polymerization was continued for further 17 hours, and then the reaction was terminated. The weight-average molecular weight was measured to be 310,000 by GPC-MALS. The product thus obtained was provided as "graft polymer 4."

Example 5

Into a reaction container similar to the one used in Example 1, 126.19 g of deionized water, 10.06 g of a 50% by mass aqueous solution of acrylamide, 9.30 g of a 65% by mass aqueous solution of diallyldimethylammonium chloride, and 0.80 g of sodium gluconate were added, and a uniform mixture was prepared. While stirring, 10.00 g of locust bean gum (manufactured by Wako Pure Chemical Industries, Ltd., the viscosity of a 2% aqueous solution at 25° C. as measured by a B type viscometer: 1350 mPa·s) were added, and then nitrogen was introduced through the nitrogen introduction pipe, and the internal temperature was adjusted at 75° C. using a constant temperature bath. Nitrogen was introduced for 30 minutes, after which 1.50 g of a 10% by mass aqueous solution of ammonium peroxodisulfate was added to initiate polymerization.

Meanwhile, 37.85 g of a 50% by mass aqueous solution of acrylamide was added to 2.70 g of a 30% by mass aqueous solution of sodium gluconate to prepare a mixture. Polymerization was performed while adding the mixture thus obtained dropwise to the system prepared as above over five hours from immediately after initiation of the reaction. After five hours, 1.50 g of a 10% by mass aqueous solution of ammonium peroxodisulfate was further added and polymerization was continued for further 17 hours, and then the reaction was terminated. The weight-average molecular weight was measured to be 1,200,000 by GPC-MALS. The product thus obtained was provided as "graft polymer 5."

Example 6

Guar gum (manufactured by MRC Polysaccharide Co., Ltd., trade name "RG500", the viscosity of a 2% aqueous solution at 25° C. as measured by a B type viscometer: 42,000 mPa·s) was swollen and dissolved in deionized water so as to give a 10% by mass guar gum solution. To the guar gum thus obtained, 1.0% by mass ammonium peroxodisulfate was added and the resulting mixture was heated to 65° C. to adjust the viscosity of a 2% aqueous solution to 8500 mPa·s. Into a reaction container similar to the one used in Example 1, 150 g of a 10% by mass guar gum solution with an adjusted molecular weight was put, and 44.22 g of deionized water, 12.05 g of a 50% by mass aqueous solution of acrylamide, 25.07 g of a 65% by mass aqueous solution of diallyldimethylammonium chloride, and 0.90 g of sodium formate were added, and a uniform mixture was prepared. Nitrogen was introduced through the nitrogen introduction pipe, and the internal temperature was adjusted at 65° C. using a constant temperature bath. Nitrogen was introduced for 30 minutes, after which 2.25 g of a 10% by mass aqueous solution of ammonium peroxodisulfate was added to initiate polymerization.

Meanwhile, 45.35 g of a 50% by mass aqueous solution of acrylamide was added to 3.00 g of a 30% by mass aqueous solution of sodium formate to prepare a mixture. Polymerization was performed while adding the mixture thus obtained dropwise to the system prepared as above over five hours from immediately after initiation of the reaction. After five hours, 2.25 g of a 10% by mass aqueous solution of ammonium peroxodisulfate further was added and polymerization was continued for further 17 hours, and then the reaction was terminated. The weight-average molecular weight was measured to be 90,000 by GPC-MALS. The product thus obtained was provided as "graft polymer 6."

Example 7

Into a reaction container similar to the one used in Example 1, 129.22 g of deionized water, 8.04 g of a 50% by mass aqueous solution of acrylamide, 16.72 g of a 65% by mass aqueous solution of diallyldimethylammonium chloride, and 0.40 g of sodium gluconate were added, and a uniform mixture was prepared. While stirring, 10.00 g of sericin (manufactured by Kashiro Sangyo, Co., Ltd., the viscosity of a 2% aqueous solution at 25° C. as measured by a B type viscometer: 16 mPa·s) were added, and then nitrogen was introduced through the nitrogen introduction pipe, and the internal temperature was adjusted at 65° C. using a constant temperature bath. Nitrogen was introduced for 30 minutes, after which 1.50 g of a 10% by mass aqueous solution of ammonium peroxodisulfate was added to initiate polymerization.

Meanwhile, 30.23 g of a 50% by mass aqueous solution of acrylamide was added to 2.00 g of a 20% by mass aqueous solution of sodium gluconate to prepare a mixture. Polymerization was performed while adding the mixture thus obtained dropwise to the system prepared as above over five hours from immediately after initiation of the reaction. After five hours, 1.50 g of a 10% by mass aqueous solution of ammonium peroxodisulfate was further added and polymerization was continued for further 17 hours, and then the reaction was terminated. The weight-average molecular weight was measured to be 30,000 by GPC-MALS. The product thus obtained was provided as "graft polymer 7."

Example 8

Into a reaction container similar to the one used in Example 1, 137.96 g of deionized water, 7.77 g of a 50% by mass aqueous solution of acrylamide, 3.54 g of an 80% by mass aqueous solution of methacryloyloxyethyltrimethylammonium chloride, and 0.35 g of sodium formate were added, and a uniform mixture was prepared. While stirring, 8.00 g of hydroxyethyl cellulose (manufactured by Wako Pure Chemical Industries, Ltd., the viscosity of a 2% aqueous solution at 25° C. as measured by a B type viscometer: 152 mPa·s) were added, and then nitrogen was introduced through the nitrogen introduction pipe, and the internal temperature was adjusted at 65° C. using a constant temperature bath. Nitrogen was introduced for 30 minutes, after which 0.80 g of a 2% by mass aqueous solution of ammonium peroxodisulfate was added to initiate polymerization.

Meanwhile, 29.23 g of a 50% by mass aqueous solution of acrylamide and 13.33 g of an 80% by mass aqueous solution of methacryloyloxyethyltrimethylammonium chloride was added to 1.75 g of a 20% by mass aqueous solution of sodium formate to prepare a mixture. Polymerization was performed while adding the mixture thus obtained dropwise to the system prepared as above over five hours from immediately after initiation of the reaction. After five hours, 0.80 g of a 2% by mass aqueous solution of ammonium peroxodisulfate was further added and polymerization was continued for further 17 hours, and then the reaction was terminated. The weight-average molecular weight was measured to be 800,000 by GPC-MALS. The product thus obtained was provided as "graft polymer 8."

Example 9

Into a reaction container similar to the one used in Example 1, 205.54 g of deionized water, 11.68 g of a 50% by mass aqueous solution of acrylamide, 5.65 g of a 75% by mass aqueous solution of acryloylaminopropyltrimethylammonium chloride, and 0.53 g of sodium formate were added, and a uniform mixture was prepared. While stirring, 12.00 g of hydroxyethyl cellulose (manufactured by Wako Pure Chemical Industries, Ltd., the viscosity of a 2% aqueous solution at 25° C. as measured by a B type viscometer: 152 mPa·s) were added, and then nitrogen was introduced through the nitrogen introduction pipe, and the internal temperature was adjusted at 65° C. using a constant temperature bath. Nitrogen was introduced for 30 minutes, after which 2.40 g of a 10% by mass aqueous solution of ammonium peroxodisulfate was added to initiate polymerization. Meanwhile, 43.94 g of a 50% by mass aqueous solution of acrylamide and 21.27 g of a 75% by mass aqueous solution of acryloylaminopropyltrimethylammonium chloride was added to 2.65 g of a 20% by mass aqueous solution of sodium formate to prepare a mixture. Polymerization was performed while adding the mixture thus obtained dropwise to the system prepared as above over five hours from immediately after initiation of the reaction. After five hours, 2.40 g of a 10% by mass aqueous solution of ammonium peroxodisulfate was further added and polymerization was continued for further 17 hours, and then the reaction was terminated. The weight-average molecular weight was measured to be 730,000 by GPC-MALS. The product thus obtained was provided as "graft polymer 9."

Example 10

Into a reaction container similar to the one used in Example 1, 204.32 g of deionized water, 5.78 g of a 50% by mass aqueous solution of acrylamide, 48.07 g of a 65% by mass aqueous solution of diallyldimethylammonium chloride, and 0.30 g of sodium formate were added, and a uniform mixture was prepared. While stirring, 15.00 g of hydroxyethyl cellulose (manufactured by Wako Pure Chemical Industries, Ltd., the viscosity of a 2% aqueous solution at 25° C. as measured by a B type viscometer: 152 mPa·s) were added, and then nitrogen was introduced through the nitrogen introduction pipe, and the internal temperature was adjusted at 65° C. using a constant temperature bath. Nitrogen was introduced for 30 minutes, after which 2.25 g of a 10% by mass aqueous solution of ammonium peroxodisulfate was added to initiate polymerization. Meanwhile, 21.73 g of a 50% by mass aqueous solution of acrylamide was added to 2.00 g of a 20% by mass aqueous solution of sodium formate to prepare a mixture. Polymerization was performed while adding the mixture thus obtained dropwise to the system prepared as above over five hours from immediately after initiation of the reaction. After five hours, 2.25 g of a 10% by mass aqueous solution of ammonium peroxodisulfate was further added and polymerization was continued for further 17 hours, and then the reaction was terminated. The weight-average molecular weight was measured to be 560,000 by GPC-MALS. The product thus obtained was provided as "graft polymer 10."

Comparative Example 1

Into a reaction container similar to the one used in Example 1, 140.85 g of deionized water, 46.15 g of a 65% by mass aqueous solution of diallyldimethylammonium chloride were added, and a uniform mixture was prepared. While stirring, 10.00 g of hydroxyethyl cellulose (manufactured by Wako Pure Chemical Industries, Ltd., the viscosity of a 2% aqueous solution at 25° C. as measured by a B type viscometer: 152 mPa·s) were added, and then nitrogen was introduced through the nitrogen introduction pipe, and the internal temperature was adjusted at 65° C. using a constant temperature bath. Nitrogen was introduced for 30 minutes, after which 1.50 g of a 10% by mass aqueous solution of ammonium peroxodisulfate were added to initiate polymerization. After five hours, 1.50 g of a 10% by mass aqueous solution of ammonium peroxodisulfate was further added and polymerization was continued for further 17 hours. Upon examining the progress of the reaction, the percentage completion was found to be approximately 40%. Thus, 1.50 g of a 10% by mass aqueous solution of ammonium peroxodisulfate was further added and polymerization was continued for further 17 hours, and then the reaction was terminated. The weight-average molecular weight was measured to be 310,000 by GPC-MALS. The product thus obtained was provided as "graft polymer 11."

Example 11

Each graft polymer from Examples 1 to 10 and Comparative Example 1 or a commercial cation polymer was provided as Ingredient B. Ingredient B was dissolved in Ingredient A in accordance with the composition as shown in Table 1, whereby shampoo liquids were prepared. The concentration of Ingredient B added and the external appearance of a shampoo having Ingredients A and B dissolved therein are shown in Table 2 and Table 3. However, the graft polymers of Example 10 and Comparative Example 1 formed an ion complex with an anionic surfactant, failing to dissolve in Ingredient A. Thus, these graft polymers were not subjected to the shampoo test. Feeling upon use of each sample as a hair shampoo was organoleptically evaluated in accordance with the method described below and evaluations were made based on the criteria shown in Table 4.

(1) Preparation of Ingredient A

Purified water was heated to 60° C., to which an anionic surfactant, a betaine surfactant, and monoethanolamide were added, followed by stirring. Thereafter, heating was stopped and 1,3-butanediol, phenoxyethanol, EDTA2Na2$H_2$O were added, followed by stirring. The resulting mixture was then cooled to room temperature.

(2) Preparation of Ingredient B

Each graft polymer and a commercial cation were dissolved in purified water at room temperature.

(3) Preparation of Shampoo Liquid

Ingredient A was heated to 60° C., to which Ingredient B was added in accordance with the composition as shown in Table 1. Thereafter, the resulting mixture was thoroughly mixed and cooled to room temperature.

(4) Evaluation Method

Five panelists tested each shampoo liquid in practical use, and organoleptically evaluated as to lather during shampooing, sleekness during shampooing, smoothness of finger combing during shampooing, slimy feeling during shampooing, rinsing fastness, friction feeling after shampooing, and smoothness of combing after shampooing. Setting the feeling upon use of a 1.0% by mass shampoo liquid of polyquaternium-10 at "average: 3", evaluations were made based on the criteria shown in Table 3. The results thus obtained are shown in Table 5. The feeling upon use of a commercial cation polymer, which is a control product, is shown in Table 6.

TABLE 1

| | Ingredient | Content |
|---|---|---|
| Ingredient A | Anionic surfactant (Taipol soft NLES-327, manufactured by Taiko Oil Chemicals Company, Ltd.) | 9.0% |
| | Betaine surfactant (Taipol soft AM-100N, manufactured by Taiko Oil Chemicals Company, Ltd.) | 6.0% |
| | Monoethanolamide | 1.5% |
| | 1,3-Butanediol | 3.0% |
| | Phenoxyethanol | 0.1% |
| | EDTA•2Na•2$H_2$O | 0.05% |
| | Purified water | 77.0-80.0% |
| Ingredient B | Graft polymer or commercial cation polymer | 0.1-2.0% |
| Total | | 100% |

(Unit: % by mass)

TABLE 2

| Name of polymer | Concentration of Ingredient B | External appearance of shampoo liquid |
|---|---|---|
| Graft copolymer 1 | 0.1% | Clear |
| | 0.2% | Clear |
| | 0.4% | Clear |
| | 0.6% | Clear |
| Graft copolymer 2 | 0.1% | Clear |
| | 0.2% | Clear |
| | 0.4% | Clear |
| | 0.6% | Clear |

TABLE 2-continued

| Name of polymer | Concentration of Ingredient B | External appearance of shampoo liquid |
|---|---|---|
| Graft copolymer 3 | 0.1% | Clear |
| | 0.2% | Clear |
| | 0.4% | Clear |
| | 0.6% | Clear |
| Graft copolymer 4 | 0.1% | Clear |
| | 0.2% | Clear |
| | 0.4% | Clear |
| | 0.6% | Clear |
| Graft copolymer 5 | 0.1% | Clear |
| | 0.2% | Clear |
| | 0.4% | Clear |
| | 0.6% | Clear |
| Graft copolymer 6 | 0.1% | Clear |
| | 0.2% | Clear |
| | 0.4% | Clear |
| | 0.6% | Clear |
| Graft copolymer 7 | 0.1% | Clear |
| | 0.2% | Clear |
| | 0.4% | Clear |
| | 0.6% | Clear |
| Graft copolymer 8 | 0.1% | Clear |
| | 0.2% | Clear |
| | 0.4% | Clear |
| | 0.6% | Clear |

TABLE 2-continued

| Name of polymer | Concentration of Ingredient B | External appearance of shampoo liquid |
|---|---|---|
| Graft copolymer 9 | 0.1% | Clear |
| | 0.2% | Clear |
| | 0.4% | Clear |
| | 0.6% | Clear |

(Unit: % by mass)

TABLE 3

| Name of polymer | Concentration of Ingredient B | External appearance of shampoo liquid |
|---|---|---|
| Polyquaternium 10 | 0.5% | Clear |
| (HC-100, manufactured | 1.0% | Clear |
| by Toho Chemical | 1.5% | Clear |
| Industry Co., Ltd.) | 2.0% | Clear |
| Polyquaternium 7 | 0.1% | Clear |
| (MERQUAT550, | 0.2% | Slightly turbid |
| manufactured by | 0.4% | Slightly turbid |
| Nalco Company) | 0.6% | Slightly turbid |

(Unit: % by mass)

TABLE 4

| Score | Lather | Sleekness during shampooing | Smoothness of finger combing during shampooing | Slimy feeling during shampooing | Rinsing fastness | Refreshing feeling after shampooing | Smoothness of combing after shampooing |
|---|---|---|---|---|---|---|---|
| 5 | Excellent | Excellent | Excellent | Not unpleasant | Very fast | Extremely refreshing | Excellent |
| 4 | Good | Good | Good | Less unpleasant | Fast | Very refreshing | Good |
| 3 | Fair | Fair | Fair | Fair | Fair | Refreshing | Fair |
| 2 | Poor | Poor | Poor | Little unpleasant | Slow | Not very refreshing | Poor |
| 1 | Very poor | Very poor | Very poor | Strongly unpleasant | Very slow | Not refreshing at all | Very poor |

TABLE 5

| Name of polymer | Concentration of Ingredient B | Lather | Sleekness during shampooing | Smoothness of finger combing during shampooing | Slimy feeling during shampooing | Rinsing fastness | Refreshing feeling after shampooing | Smoothness of combing after shampooing |
|---|---|---|---|---|---|---|---|---|
| Graft polymer 1 | 0.1% | 3.0 | 3.0 | 3.2 | 4.4 | 4.6 | 4.6 | 3.0 |
| | 0.2% | 3.2 | 3.2 | 3.4 | 4.4 | 4.6 | 4.6 | 3.0 |
| | 0.4% | 3.2 | 3.4 | 3.6 | 4.2 | 4.6 | 4.6 | 3.2 |
| | 0.6% | 3.2 | 3.6 | 3.8 | 4.0 | 4.6 | 4.6 | 3.4 |
| Graft polymer 2 | 0.1% | 3.0 | 3.4 | 3.6 | 4.2 | 4.0 | 3.8 | 4.0 |
| | 0.2% | 3.2 | 3.8 | 3.8 | 4.2 | 4.0 | 3.8 | 4.4 |
| | 0.4% | 3.4 | 4.2 | 4.2 | 4.2 | 4.0 | 3.6 | 4.8 |
| | 0.6% | 3.4 | 4.6 | 4.4 | 4.2 | 4.0 | 3.6 | 5.0 |
| Graft polymer 3 | 0.1% | 3.0 | 3.2 | 3.0 | 4.6 | 4.8 | 5.0 | 3.0 |
| | 0.2% | 3.2 | 3.4 | 3.0 | 4.6 | 4.8 | 5.0 | 3.2 |
| | 0.4% | 3.2 | 3.6 | 3.2 | 4.6 | 4.8 | 4.8 | 3.4 |
| | 0.6% | 3.2 | 3.8 | 3.4 | 4.6 | 4.8 | 4.8 | 3.6 |
| Graft polymer 4 | 0.1% | 3.0 | 3.6 | 3.8 | 4.2 | 4.0 | 3.8 | 4.0 |
| | 0.2% | 3.4 | 4.0 | 4.0 | 4.2 | 4.0 | 3.8 | 4.4 |
| | 0.4% | 3.6 | 4.4 | 4.2 | 4.2 | 4.0 | 3.6 | 4.8 |
| | 0.6% | 3.8 | 4.8 | 5.0 | 4.2 | 4.0 | 3.6 | 5.0 |
| Graft polymer 5 | 0.1% | 3.0 | 3.0 | 3.4 | 4.6 | 4.6 | 4.6 | 3.0 |
| | 0.2% | 3.2 | 3.2 | 3.6 | 4.4 | 4.6 | 4.6 | 3.2 |
| | 0.4% | 3.2 | 3.4 | 3.8 | 4.4 | 4.6 | 4.4 | 3.4 |
| | 0.6% | 3.4 | 3.4 | 4.0 | 4.2 | 4.4 | 4.4 | 3.4 |

TABLE 5-continued

| Name of polymer | Concentration of Ingredient B | Lather | Sleekness during shampooing | Smoothness of finger combing during shampooing | Slimy feeling during shampooing | Rinsing fastness | Refreshing feeling after shampooing | Smoothness of combing after shampooing |
|---|---|---|---|---|---|---|---|---|
| Graft polymer 6 | 0.1% | 3.0 | 3.2 | 3.4 | 4.2 | 4.0 | 4.0 | 4.0 |
| | 0.2% | 3.2 | 3.6 | 3.8 | 4.2 | 4.0 | 3.8 | 4.4 |
| | 0.4% | 3.4 | 4.0 | 4.2 | 4.2 | 4.0 | 3.6 | 4.6 |
| | 0.6% | 3.6 | 4.4 | 4.6 | 4.2 | 4.0 | 3.6 | 4.8 |
| Graft polymer 7 | 0.1% | 3.0 | 3.2 | 3.2 | 4.0 | 4.0 | 4.0 | 4.0 |
| | 0.2% | 3.4 | 3.4 | 3.4 | 4.0 | 4.0 | 4.0 | 4.2 |
| | 0.4% | 3.6 | 3.6 | 3.8 | 4.0 | 4.0 | 3.8 | 4.2 |
| | 0.6% | 4.0 | 3.6 | 4.0 | 4.0 | 4.0 | 3.8 | 4.4 |
| Graft polymer 8 | 0.1% | 2.8 | 3.0 | 3.0 | 3.0 | 3.0 | 3.0 | 3.0 |
| | 0.2% | 3.1 | 3.3 | 3.2 | 3.2 | 3.2 | 3.4 | 3.2 |
| | 0.4% | 3.2 | 3.4 | 3.2 | 3.2 | 3.2 | 3.4 | 3.2 |
| | 0.6% | 3.2 | 3.6 | 3.4 | 3.2 | 3.4 | 3.4 | 3.4 |
| Graft polymer 9 | 0.1% | 3.0 | 3.2 | 3.2 | 3.2 | 3.2 | 3.2 | 3.2 |
| | 0.2% | 3.4 | 3.4 | 3.4 | 3.2 | 3.2 | 3.2 | 3.2 |
| | 0.4% | 3.4 | 3.6 | 3.4 | 3.4 | 3.4 | 3.2 | 3.2 |
| | 0.6% | 3.6 | 3.6 | 3.6 | 3.4 | 3.4 | 3.4 | 3.4 |

(Unit: % by mass)

TABLE 6

| Name of polymer | Concentration of Ingredient B | Lather | Sleekness during shampooing | Smoothness of finger combing during shampooing | Slimy feeling during shampooing | Rinsing fastness | Refreshing feeling after shampooing | Smoothness of combing after shampooing |
|---|---|---|---|---|---|---|---|---|
| Polyquaternium 10 | 0.5% | 1.8 | 1.4 | 1.8 | 3.2 | 3.2 | 3.0 | 2.0 |
| (HC-100, manufactured | 1.0% | 3.0 | 3.0 | 3.0 | 3.0 | 3.0 | 3.0 | 3.0 |
| by Toho Chemical | 1.5% | 3.0 | 3.0 | 3.2 | 2.0 | 2.8 | 2.4 | 3.0 |
| Industry Co., Ltd.) | 2.0% | 3.0 | 3.0 | 3.4 | 1.2 | 2.4 | 1.6 | 3.0 |
| Polyquaternium 7 | 0.1% | 3.0 | 3.0 | 3.2 | 2.2 | 2.6 | 2.8 | 3.4 |
| (MERQUAT550, | 0.2% | 2.8 | 3.2 | 3.6 | 1.8 | 2.4 | 2.4 | 3.6 |
| manufactured by | 0.4% | 2.4 | 3.4 | 3.6 | 1.4 | 2.2 | 2.0 | 3.8 |
| Nalco Company) | 0.6% | 2.4 | 3.4 | 3.8 | 1.0 | 1.6 | 1.8 | 3.8 |

(Unit: % by mass)

As apparent from Table 5 and Table 6, it was confirmed that polyquaternium 10 had to be added in an amount of at least approximately 1.0% by mass in order to attain a high conditioning effect, whereas graft polymers 1 to 9 needed to be added in an amount of approximately 0.1% by mass to attain favorable effects. When polyquaternium-7 was added in an amount of 0.2% by mass or more, a shampoo liquid became turbid and gave a strong slimy feeling upon use, whereas graft polymers 1 to 9 were confirmed not to give sliminess even when added in a large amount. It was confirmed that graft polymers 1, 3, and 5 were quickly rinsed off and gave a strong refreshing feeling after use, and graft polymers 2, 4, 6, and 7 produced sleekness upon use and an intensely moisturized feeling after application. While any of the graft polymers 1 to 9 had a better effect than did a commercial polymer, among them graft polymers 1 to 7 were confirmed to have a particularly excellent effect.

Example 12

Each graft polymer from Examples 4 and 10 and Comparative Example 1 and a commercial cation polymer were dissolved in accordance with the composition as shown in Table 7, whereby a conditioner liquid was prepared. Each sample was organoleptically evaluated for feeling upon use as a hair conditioner in accordance with the method described below and evaluations were made based on the criteria shown in Table 8.

(1) Preparation of Ingredient A

A cationic surfactant, stearyl alcohol, and glutamic acid were stirred at 75° C. and melted. Subsequently, deionized water heated to 75° C. was added, and the contents were further dissolved.

(2) Preparation of Ingredient B

Each graft polymer and a commercial cation copolymer were dissolved in purified water at room temperature.

(3) Preparation of Conditioner Liquid

Ingredient A was heated to 75° C., to which Ingredient B was added in accordance with the composition as shown in Table 7. Thereafter, the resulting mixture was thoroughly mixed and cooled to room temperature.

(4) Evaluation Method

Five panelists tested each conditioner liquid in practical use. A shampoo was prepared in accordance with the composition as shown in Table 1 except for eliminating the polymer, and the hair was washed with the shampoo thus prepared before application of the conditioner. After hair washing, organoleptic evaluations were conducted for each conditioner as to suppleness upon application, sleekness upon application, sleekness during rinsing the hair, smoothness of finger combing after towel drying, and smoothness of finger combing right after drying, smoothness right after drying, and moisturized feeling of the hair on the day after drying. Organoleptic evaluations were made based on the criteria shown in Table 8. In conducting organoleptic evaluation, the feeling upon use of a conditioner prepared without a cation polymer was set at "average: 3." The feeling upon use of a conditioner without a polymer, each graft polymer from Examples 4, 10, and Comparative Example 1, or the feeling upon use of a commercial cation polymer, which was a control product, are shown in Table 9.

TABLE 7

| | | Content |
|---|---|---|
| Ingredient A | Cationic surfactant (Quartamin 86W, manufactured by Kao Corporation) | 2.0% |
| | Stearyl alcohol | 5.0% |
| | glutamic acid | 0.2% |
| | Purified water | Balance |
| Ingredient B | Graft polymer or commercial cation polymer | 0.5% |
| Total | | 100% |

(Unit: % by mass)

TABLE 8

| | Upon application | | Upon rinsing | After towel drying | Hair right after drying | | Day after drying |
|---|---|---|---|---|---|---|---|
| Score | Suppleness | Sleekness | Sleekness of hair | Smoothness of finger combining | Smoothness of finger combining | Smoothness | Moisturized feeling of hair |
| 5 | Excellent | Excellent | Excellent | Excellent | Very fast | Extremely smooth | Extremely moisturized |
| 4 | Good | Good | Good | Good | Fast | Very smooth | Very moisturized |
| 3 | Fair | Fair | Fair | Fair | Fair | Smooth | Moisturized |
| 2 | Poor | Poor | Poor | Poor | Slow | Not very smooth | Not very moisturized |
| 1 | Very poor | Very poor | Very poor | Very poor | Very slow | Not smooth at all | Not moisturized at all |

TABLE 9

| | Upon application | | Upon rinsing | After towel drying | Hair right after drying | | Day after drying |
|---|---|---|---|---|---|---|---|
| Name of polymer | Suppleness | Sleekness | Sleekness of hair | Smoothness of finger combining | Smoothness of finger combining | Smoothness | Sleekness |
| Non-polymer formulation | 3.0 | 3.0 | 3.0 | 3.0 | 3.0 | 3.0 | 3.0 |
| Graft polymer 4 | 4.4 | 4.2 | 3.6 | 4.4 | 4.6 | 4.8 | 4.6 |
| Graft polymer 10 | 4.0 | 3.8 | 3.6 | 4.2 | 4.0 | 4.2 | 4.2 |
| Graft polymer 11 | 3.2 | 3.0 | 3.2 | 3.0 | 3.0 | 2.6 | 2.6 |
| Polyquaternium-6 (MERQUAT100, manufactured by Nalco Company) | 3.2 | 3.0 | 3.6 | 3.0 | 3.2 | 2.2 | 2.4 |

From Table 9, it was confirmed that a high conditioning effect was exhibited when graft polymers 4 and 10 were added to a conditioner. The effect thus obtained was higher than the effects exhibited by graft polymer 11 prepared without using a nonionic monomer (Comparative Example 1) and by polyquaternium-6, which was a commercial product. Further, it was confirmed that the hair cosmetic preparation according to the present embodiment was highly effective in keeping the hair in a favorable condition right after drying and the day after drying, and also that it had an effect of making the hair after drying soft to the touch.

Example 13

Each graft polymer from Examples 4 and 10 and Comparative Example 1 and a commercial cation polymer were each dissolved at a concentration of 0.5% by mass. The solutions thus obtained were used as a hair styling agent having a curl retention ability, and the feeling upon use was organoleptically evaluated in accordance with the method described below.

Evaluation Method

Into the 0.5% by mass aqueous solution having each of the aforementioned polymer dissolved therein, a 35 cm-long hair tress was immersed for 15 seconds. The hair was removed, from which water was lightly drained off. The hair was then rolled around a hair curler with a diameter of 2 cm and dried for 15 minutes using a hot dryer. Then, while the hair was still rolled around the hair curler, it was placed in a constant temperature room at 26° C. and a humidity of 60% by mass for 30 minutes. Thereafter, the hair was removed from the hair curler and the length from the root to the tip of the hair tress was measured. The length thus measured was provided as L0. The hair after measurement was hung and further left for 30 minutes. Thereafter, the length of the entire hair was measured and the value thus obtained was provided as L1. The hair after measurement was combed five times and the length was measured again, which was recorded as L2. Further, the feeling of the hair after use of the hair styling agent was simultaneously evaluated. Curl retention ability was evaluated by comparing L0, L1, and L2 values. L0, L1, and L2 values of a hair tress immersed only in water were measured, which were used as blank in the evaluation. The blank values and L0, L1, and L2 values of each graft polymer from Examples 4, 10 and Comparative Example 1, and a commercial cation polymer, which was a control product, as well as the feeling after use of these products are shown in Table 10.

TABLE 10

| | Blank | Graft polymer 4 | Graft polymer 10 | Graft polymer 11 | Polyquaternium 6 (MERQUAT100, manufactured by Nalco Company) | Polyquaternium 7 (MERQUAT550, manufactured by Nalco Company) | Polyquaternium 10 (HC-100, manufactured by Toho Chemical Industry Co., Ltd.) |
|---|---|---|---|---|---|---|---|
| L0 (cm) | 24 | 17 | 15 | 26 | 24 | 19 | 23 |
| L1 (cm) | 27 | 22 | 22 | 28 | 28 | 23 | 26 |
| L2 (cm) | 30 | 24 | 25 | 29 | 29 | 26 | 28 |
| Feeling upon use | Dry | Smooth | Smooth | Slightly sticky | Sticky | Sticky | Dry |

As shown in Table 10, any of L0, L1, and L2 values was small in graft polymers 4 and 10. From the above results, it was confirmed that the hair cosmetic preparation according to the present embodiment had excellent curl production ability and retention ability, and that the curl thus produced was resistant against combing. Graft polymer 11 prepared without a nonionic monomer (Comparative Example 1) had almost no curl production ability. As to the feeling after use, the hair treated with blank was dry and unmanageable with fly-away hair, and stickiness associated with the polymer was left on the hair treated with polyquaternium-6 and polyquaternium-7, and further, the hair treated with polyquaternium-10 solidified into bundles with a stiff and dry feeling. In contrast, the hair treated with the hair cosmetic preparation according to the present embodiment was soft to the touch, and it was confirmed that the hair cosmetic preparation according to the present embodiment can give the hair moisture and a smooth feeling.

INDUSTRIAL APPLICABILITY

The additive for the hair cosmetic preparation and the hair cosmetic preparation containing the additive according to the present invention can give a supple feel to the finished hair. They can be used in a wide range of application including, for example, a shatpoo, a rinse, various conditioners, a hair styling agent, a perm lotion, and a hair dye.

The present application is based on Japanese Patent Application filed on Aug. 8, 2008 (Japanese Patent Application No. 2008-204911), the content of which is incorporated herein by reference.

What is claimed is:

1. An additive for a hair cosmetic preparation comprising:

at least one of an anionic surfactant, a cationic surfactant, a betaine surfactant, or a nonionic surfactant; and a graft copolymer obtainable by graft-copolymerizing a cationic water-soluble monomer and a nonionic water-soluble monomer in an aqueous solution comprising a natural polymer having an OH group and/or a natural polymer derivative having an OH group, wherein:

the cationic water-soluble monomer is at least diallyldimethylammonium chloride, and the nonionic water-soluble monomer is at least acrylamide, the natural polymer is one or more selected from the group consisting of guar gum, locust bean gum, and sericin, and the natural polymer derivative is one or more selected from the group consisting of hydroxyethyl cellulose, hydroxypropyl cellulose, hydroxypropyl methylcellulose, and hydroxypropyl guar gum.

2. The additive for the hair cosmetic preparation according to claim 1, wherein a content of the cationic water-soluble monomer in the water-soluble monomers is from 5 to 90 mol %, and a content of the nonionic water-soluble monomer in the water-soluble monomers is from 10 to 95 mol %.

3. The additive for the hair cosmetic preparation according to claim 1 or 2, wherein a viscosity of a 2% aqueous solution of the natural polymer or the natural polymer derivative is 20,000 mPa·s or less at 25° C.

4. The additive for the hair cosmetic preparation according to claim 1 or 2, wherein a mass ratio (A/B) of (A) a total amount of the natural polymer and/or the natural polymer derivative to (B) a total amount of the water-soluble monomer is from 5/95 to 80/20.

5. The additive for the hair cosmetic preparation according to claim 1 or 2, wherein a total concentration of the natural polymer, the natural polymer derivative, and the water-soluble monomer in a reaction solution of the graft copolymer is from 10 to 50% by mass.

6. The additive for the hair cosmetic preparation according to claim 1 or 2, wherein a weight-average molecular weight of the graft copolymer is from 10,000 to 3,000,000.

7. The additive for the hair cosmetic preparation according to claim 1 or 2, wherein the graft copolymer is obtainable by performing a polymerization reaction at 50° C. or higher using a persulfate as an initiator.

8. The additive for the hair cosmetic preparation according to claim 1, wherein the graft copolymer is obtainable by performing graft copolymerization while adding at least a part of an amount of the acrylamide continuously or sequentially.

9. A hair cosmetic preparation comprising the additive for the hair cosmetic preparation according to claim 1 or 2.

10. The hair cosmetic preparation according to claim 9, wherein the hair cosmetic preparation is a rinse, a conditioner, a treatment agent, a hair styling agent, a perm lotion, or a hair dye.

11. The hair cosmetic preparation according to claim 9, wherein the hair cosmetic preparation is a shampoo, and the content of the cationic water-soluble monomer in the water-soluble monomers is within a range of from 5 to 30 mol %.

12. A method for producing an additive for a hair cosmetic preparation comprising the steps of:

dissolving a natural polymer having an OH group and/or a natural polymer derivative having an OH group in water to prepare an aqueous solution, wherein the natural polymer is one or more selected from the group consisting of guar gum, locust bean gum, and sericin and the natural polymer derivative is one or more selected from the group consisting of hydroxyethyl cellulose, hydroxypropyl cellulose, hydroxypropyl methylcellulose, and hydroxypropyl guar gum; and graft-copolymerizing acrylamide and diallyldimethyl ammonium chloride in the aqueous solution.

13. The method for producing the additive for the hair cosmetic preparation according to claim 12, wherein a chain transfer agent is added to the aqueous solution in the step of graft copolymerization.

14. The method for producing the additive for the hair cosmetic preparation according to claim 12 or 13, wherein a persulfate is added to the aqueous solution as an initiator in the step of graft copolymerization.

15. The method for producing the additive for the hair cosmetic preparation according to claim 12 or 13, wherein at least a part of an amount of the acrylamide is continuously or sequentially added to the aqueous solution in the step of graft copolymerization.

16. The method for producing the additive for the hair cosmetic preparation according to claim 12, wherein the anionic surfactant is a N-fatty acid acyl-L-glutamate, a N-fatty acid-N-methyltaurate, a salt of N-fatty acid sarcosine condensation product, or a N-acyl fatty acid-N-methyl-β-alanine salt.

17. The method for producing the additive for hair cosmetic preparation according to claim 16, wherein the anionic surfactant is sodium lauroyl methylalanine, triethanolamine cocoyl glutamate, sodium N-lauryl-L-glutamate, triethanolamine N-coconut oil fatty acid-L-glutamate, sodium N-myristic acid acyl-L-glutamate, sodium N-mixed fatty acid acyl-L-glutamate, sodium methyltaurate laurate, sodium coconut oil fatty acid methyltaurate, sodium lauroylsarcosine, sodium cocoylsarcosine, d sodium acylsarcosine, acyl glutamate, sodium acyl-β-alanine, acyl taurate, lauryl sulfate, polyoxyethylene lauryl ether sulfate, sodium N-coconoyl-N-methyl-β-alanine or sodium N-myristoyl-N-methyl-β-alanine.

18. The method for producing the additive for the hair cosmetic preparation according to claim 12, wherein the cationic surfactant is lauryltrimethylammonium chloride, stearyltrimethylammonium chloride, distearyldimethylammonium chloride, or stearyldimethylbenzylammonium chloride.

19. The method for producing the additive for the hair cosmetic preparation according to claim 12, wherein the betaine surfactant is betaine lauryldimethylaminoacetate, cocoacidopropyl betaine, dimethyllauryl betaine, bis(2-hydroxyethyl)lauryl betaine, coconut oil fatty acid amidopropyl betaine, sodium cocoamphoacetate, cyclohexyl lauryl amine oxide, dimethyl lauryl amine oxide, bis(2-hydroxyethyl)lauryl amine oxide, oleyl betaine, stearyl betaine, myristyl betaine, or stearyl dihydroxyethyl betaine.

20. The method for producing the additive for the hair cosmetic preparation according to claim 12, wherein the nonionic surfactant is glyceryl monostearate, sorbitan monopalmitate, polyoxyethylene cetyl ether, polyoxyethylene sorbitan monolaurate, sorbitan fatty acid ester, glycerol fatty acid ester, polyoxyethylene sorbitan fatty acid ester, polyethylene glycol fatty acid ester, polyoxyethylene alkyl ether, polyoxyethylene alkylphenyl ether, polyoxyethylene castor oil, polyoxyethylene hydrogenated castor oil, fatty acid alkanolamide, stearic acid diethanolamide, coconut oil fatty acid diethanolamide, sorbitan sesquioleate, or polyoxyethylene stearyl ether.

* * * * *